(12) United States Patent
Brancato et al.

(10) Patent No.: US 6,787,572 B2
(45) Date of Patent: Sep. 7, 2004

(54) USE OF UBIQUINONE Q10 FOR THE LOCAL TREATMENT AND PREVENTION OF POST-SURGICAL OPHTHALMOLOGIC PATHOLOGIES

(75) Inventors: Rosario Brancato, Florence (IT); Sergio Capaccioli, Florence (IT); Marco Fabrizio Saettone, Viareggio LU (IT); Nicola Schiavone, Florence (IT)

(73) Assignee: Giuseppe Simonelli, Rome (IT)

( * ) Notice: Subject to any disclaimer, the term of this patent is extended or adjusted under 35 U.S.C. 154(b) by 14 days.

(21) Appl. No.: 09/901,320

(22) Filed: Jul. 9, 2001

(65) Prior Publication Data

US 2003/0236239 A1 Dec. 25, 2003

Related U.S. Application Data

(63) Continuation-in-part of application No. PCT/IT00/00434, filed on Oct. 30, 2000.

(30) Foreign Application Priority Data

Nov. 25, 1999 (IT) .................................... RM99A000719

(51) Int. Cl.[7] .............................................. A61K 31/12
(52) U.S. Cl. ...................... 514/690; 514/941; 424/486
(58) Field of Search ......................... 424/486; 514/690, 514/941

(56) References Cited

U.S. PATENT DOCUMENTS 5,912,272 A * 6/1999 Hoppe ........................ 514/678

FOREIGN PATENT DOCUMENTS

| GB | 2 301 775 | 12/1996 |
|---|---|---|
| WO | 99/11241 | * 3/1999 |
| WO | WO 00/23069 | 4/2000 |
| WO | WO 00/57871 | 10/2000 |

OTHER PUBLICATIONS

R. Brancato, et. al, "Prevention of corneal keratocyte apoptosis after argon fluoride excimer laser irradiation with the free radical scavenger ubiquinone Q10," *European Journal of Ophthalmology*, (Jan.–Mar. 2000) 10(1) pp. 32–38.

M. Kuwayama, "Experimental Studies on Antioxidative Effect on Coenzyme $Q_{10}$ on the Retina," *Nagoya Medical Journal*, (1984) 29, No. 3–4, pp. 137–148 (XP–000993571).

Chida, M., et al., "In vitro Testing of Antioxidants and Biochemical End–Points in Bovine Retinal Tissue," *Ophthalmic Research* (Nov. 1999), 31, No. 6, pp. 407–415 (XP–000993569).

Feher J. et al., "Coenzyme Q10 improves visual functions in retinitis pigmentosa," *Clinica Oculistica e Patologia Oculare* (1996) 17, No. 1, pp. 31–33 (XP–000993575).

Database WPI, Section Ch, Week 198417, Derwent Publications LTDI, London, GB; AN 1984–104277 (XP–002167282), JP 59047202.

* cited by examiner

Primary Examiner—Sandra Saucier
(74) Attorney, Agent, or Firm—Leffert Jay & Polglaze, P.A.

(57) ABSTRACT

In the treatment of ophthalmologic pathologies in general and in particular in the treatment and prevention of side-effects on eye following photorefractive therapy (PRK), laser-assisted in situ keratomileusis (LASIK) and exposure to solar light and ultraviolet radiation, ubiquinone Q10 is utilized in a collyrium pharmaceutical preparation for ocular topical administration thereof.

13 Claims, 10 Drawing Sheets

A) laser 193 nm 48 mJ/cm$^2$ + Q10

B) laser 193 nm 48 mJ/cm$^2$ − Q10

C) untreated

USE OF UBIQUINONE Q10 FOR THE LOCAL TREATMENT AND PREVENTION OF POST-SURGICAL OPHTHALMOLOGIC PATHOLOGIES

This is a CIP of PCT/IT00/00484, filed Oct. 30, 2000.

DESCRIPTION

1. Field of the Invention

The present invention refers to the use of quinone Q10 (ubiquinone) as active principle to be used in a pharmaceutical composition for ocular topical use for the treatment of ophthalmologic pathologies and for the prevention of the undesired side-effects in the cornea, following a treatment of refractive surgery with excimer laser and exposition to ultraviolet radiation of solar light and other sources. By way of example, under refractive surgery the photorefractive keratectomy (PRK) and the laser-assisted in situ keratomileusis (LASIK) are to be meant.

2. Background of the Invention

In the last few years a new type of surgical technique, the photorefractive keratectomy (PRK) correcting the refractive vices, such as myopia, hypermetropia and astigmatism by the use of an excimer laser has become popular and spread. This surgical procedure provides a first step of corneal disepithelization which allows, even if with different techniques, the removal of the first corneal layer which is the epithelium and the exposure of the underneath corneal stroma.

The excimer laser acts through a photoablative action exactly at the level of the frontal stromal surface by causing the remodelling thereof. This involves in the last analysis a remodelling of the frontal corneal surface since the epithelium reforming during the first days after operation follows the profile of the photoablated frontal stromal surface.

The problems connected to the PRK are represented by the possible undesired side-effects reducing the possible regression of the refractive outcome and, or, the formation of a small corneal haze which, if present in great quantity, causes a serious quantitative and qualitative decay in vision functionality, in this case not corregible even with glasses. The regression and the haze have both an etiology due to a plurality of factors.

The first factors are of individual character (genetic predisposition) and as such are not influenceable. The type of photoablative mechanism and the size of the photoablated area are then important; wider and more regular ablation areas, in fact, seem to increase the stability of the refractive outcome. The improvement of photoablative technique, however, is related to the excimer laser technique.

The last important aethiologic factor is linked to the apoptosis role. (Wilson S E, et al., Exp. Eye Res., 1996, 62:325–328; Helena B C, Inv. Ophthal. & Visual Science, 1988,39:276–283).

The apoptosis is a programmed cell death which, contrary to usual necrotic processes, is accompanied by a poor inflammatory response and by a failure in releasing the cell degradation components which otherwise would cause damage to adjacent tissue. In the cornea an apoptosis of stromal keratocytes has been observed both following herpes simplex infections, and in response to an epithelial insult such as the one performed in a photorefractive keratectomy operation during the first corneal disepithelization step. This disepithelization, whether it occurs by mechanical action, or by other technique, involves the release of cytokines (for examples interleukin-1) by damaged epithelial cells, which bond to underneath stromal keratocytes by then mediating the apoptosis thereof. The programmed cell death of these stromal keratocytes involves an activation of the adjacent keratocytes aiming at repopulating the frontal stroma and it is associated to an increased deposition of collagen and to a disorganization thereof, both phenomena considered responsible for the haze appearance and for the regression after photorefractive keratectomy operation (for a review see Wilson S E, J. Refractive Surgery, 1997, 13:171–175). The apoptosis role in a wide range of ocular pathologies has been widely demonstrated (see Capaccioli S. et al., in Bisantis C. and Carella G. "Vascular systems of the optic nerve and perioptic area." I.N.C Editor, Rome, Italy, 1998)

As it is known, the agents triggering the apoptosis are various and can be of chemical (for example genotoxic drugs), physical (radiations, mechanical insult) or biological (for example virus) nature. (Capaccioli et al., in: "Monografie della Società Italiana di Oftalmologia", Publishing house I.N.C., Rome, 1998).

As far as the ultraviolet radiation is concerned, it is ascertained by now that, in refractive keratectomy-operated patients, they induce at corneal level oxidizing processes involved both in forming "haze" and regression. In fact, in PRK-and-LASIK-operated patients, there is often the detection of a higher haze incidence at the end of the summer season, that is at the end of that year period wherein the exposure to solar radiation is maximum. These oxidizing processes involve the release of free radicals already demonstrated in laboratory preparations of ephitelium of test animals treated with excimer laser, free radicals which are potentially able to trigger the apoptosis process and direct cell damage.

The quinone Q10 plays an essential role in nature since it belongs to the mitochondrial transportation chain of electrons and it is known as an effective antioxidant.

SUMMARY OF THE INVENTION

The problem the present invention is based upon is then to provide a drug to oppose the apoptosis of corneal stromal keratocytes in the photorefractive keratectomy (PRK and LASIK), as well as to reduce the oxidizing processes induced by exposition and ultraviolet radiation of the solar light.

Therefore, it is an object of the present invention the use of the ubiquinone Q10 coenzyme, in the form of collyrium for topical ophthalmic use, to manufacture a drug for the treatment of ocular pathologies in general and, in particular, effective in the prevention and treatment of corneal haze following to corneal trauma, general surgery and refractive surgery; to prevent the regression of corrective effects after refractive surgery performed by conventional surgery or by laser radiation; to protect the eye against damage determined by radiation of solar light and by ultraviolet radiation.

Furthermore, the topical ophthalmic use of the ubiquinone Q10 for the pathology prevention and treatment, or for incidental or post-surgery trauma, of the camera frontal bulbi, including iris and crystalline, is included in the scope of the invention. More particularly, it is another object of the present invention a formulation in the form of collyrium and a process for the preparation thereof for ophthalmical administration of ubiquinone, for the cornea protection against the apoptosis of corneal stromal keratocytes which would trigger following treatment of refractive and/or excimer laser surgery and exposure to solar ultraviolet radiation.

It is known that apoptosis is a phenomenon of programmed cell death and, as such, characterized by very precise signalling routes inside the cell. Despite fundamental events have been up to now detected and grouped into virtual operating compartments (initiator, modulator, effector compartment) the precise molecular mechanisms being at the base thereof are extremely complicated, and the understanding thereof is up to now widely full of gaps. It is sure that whereas the modulator and effector compartment may be linked to a limited number of alternative signalling routes, the initiator compartment responds to a plurality of stimuli quite different among them, even if all of them are of potentially apoptotic nature. Among them, biological agents, including the virus, the hypoxia and a variety of chemical and physical agents including genotoxic agents, oxidant agents, exciting, ionizing and electromagnetic radiations, mechanical insults, stimulus by kitocynes, defect in trophic factors, etc., have been detected.

Even if the Q10 antioxidant properties have been well known for some time, the characterization thereof as agent having influence on the apoptosis of corneal stromal keratocytes in the photorefractive keratectomy is not known in the current state of art. In fact, there is exclusively indirect evidence about a Q10 involvement in the apoptosis mechanism. For example, if vehiculated in the serum, the Q10 has resulted to bring benefit in the therapy of reperfusion ischemia insult, a pathology wherein the apoptosis is well-known involved (Sharov et al., Am J. Pathol. 148 (1):141–9, 1996). However, in this pathology it is believed that the Q10 role is also to maintain integral the electrons transport chain in order to produce an ATP quantity sufficient for an optimum cardiac activity. Therefore, the Q10 role would be generally considered not only as an antioxidant molecule but also as key component of the respiratory chain, wherein this coenzyme participates as component of even three multienzymatic complexes, process which is reflected in the production of chemical energy in the form of ATP.

A third role the ubiquinone has recently resulted to play is to regulate the so-called micropore of mitochondrial permeability transition (Permeability Transition Pore, PTP) present in the inner mitochondrial membrane, wherein the Q10 inserts by bonding to a specific bonding place thereof. The functional status of the above-mentioned micropore is regulated by the complex I of the respiratory chain the Q10 is part of. At this level the Q10 acts by inhibiting the micropore opening, an early event of the apoptotic programme since it enables the cytochrome emission into the cytoplasm and the bonding thereof to APAFI which triggers the caspase activation process (Fontaine E. et al. J. Biol. Chem. 271:6746–6751, 1998).

What has been above described does not enable to assert that what has been observed in the cardiac pattern is tout court extendible to the corneal pattern.

Hereinafter the only known work is reported wherein the Q10 is directly associated to a molecule involved in the signalling route of the apoptotic process (Barroso M. P. et al, J. Bionerg. Biomembr., 1997, 29:259–67). In fact, it seems that the Q10 present in the plasmatic membrane decreases the ceramide levels, degradation product of the sphyngomyelin and known transducer of the apoptotic signal.

By referring to the PRK, even if it has been ascertained that the undesired effects of the technique are largely due to the apoptotic death of cells, the immediate effects of excimer laser on/the cytoxicity mechanisms thereof are not known.

It has been demonstrated that other antioxidants such as the ascorbic acid, the pyrrolidinditiocarbamate (PDTC), the Vitamin E, and likes, have contrasting effects on the apoptosis induced by various stimuli. For example the ascorbic acid has demonstrated to be effective in the inhibition of the apoptosis induced by oxidant stress with quite high concentrations, (Witenberg B et al., Biochem. Pharmacol., 1999, 57:823–32) but the derivatives thereof have demonstrated to be toxic in presence of $H_2O_2$ (Iwasaka K., Biochem. Anticancer Res., 1998, 18:4333–7).

The PDTC has resulted to protect against apoptosis induced by Tumor Necrosis Factor (TNF) (Higuchi M., et al. Oncogene, 1998, 17:2515–2524), but, as Vitamin E, it has resulted to induce apoptosis in a cellular line of the rectum cancer (CRC) (Chinery R, et al. Nat. Med. 1997, 11:1233–41).

Therefore, based upon the antioxidant features thereof only, it could not be foreseen that the use of Q10 as preventive and therapeutic agent in the corneal refractive surgery could have an advantageous effect in the prevention and treatment of the undesired side-effects in the photorefractive surgery (PRK and LASIK) and in the exposure to ultraviolet radiation.

Similarly, it could not be foreseen to which extent the use of Q10 may protect cells against apoptosis in those ophthalmologic diseases wherein this cell death process seems to play a key role in the pathogenetic mechanisms.

On the other side, the fact that for the Q10 there are no data about cytotoxic effects of the concentrations up to now utilized in vitro researches, is in favour of the drug harmlessness with respect to toxic effects.

EXPERIMENTAL REPORT

It has been experimented in laboratory the Q10 protective effect against apoptosis and necrosis induced by ultraviolet radiation (both with 193 nm ArF excimer laser and with 254 nm radiation) on rabbit corneal keratocyte cultures. The apoptosis has been evaluated by means of early and late markers such as analysis of the cytoplasm redox status (malonaldehyde assay), ATP levels, confocal microscopy and transmission electronics, gene p53 expression, qualitative/quantitative analysis of cell morphological changes by means of videomicroscopy at intervals.

The doses to be utilized should be in the range between 2 $\mu M$ and 500 $\mu M$, preferably 10 $\mu M$.

Furthermore, a preparation acceptable from the pharmaceutical point of view for the topical administration as Q10 collyrium has been devised In the drawings.

Figure 5A:
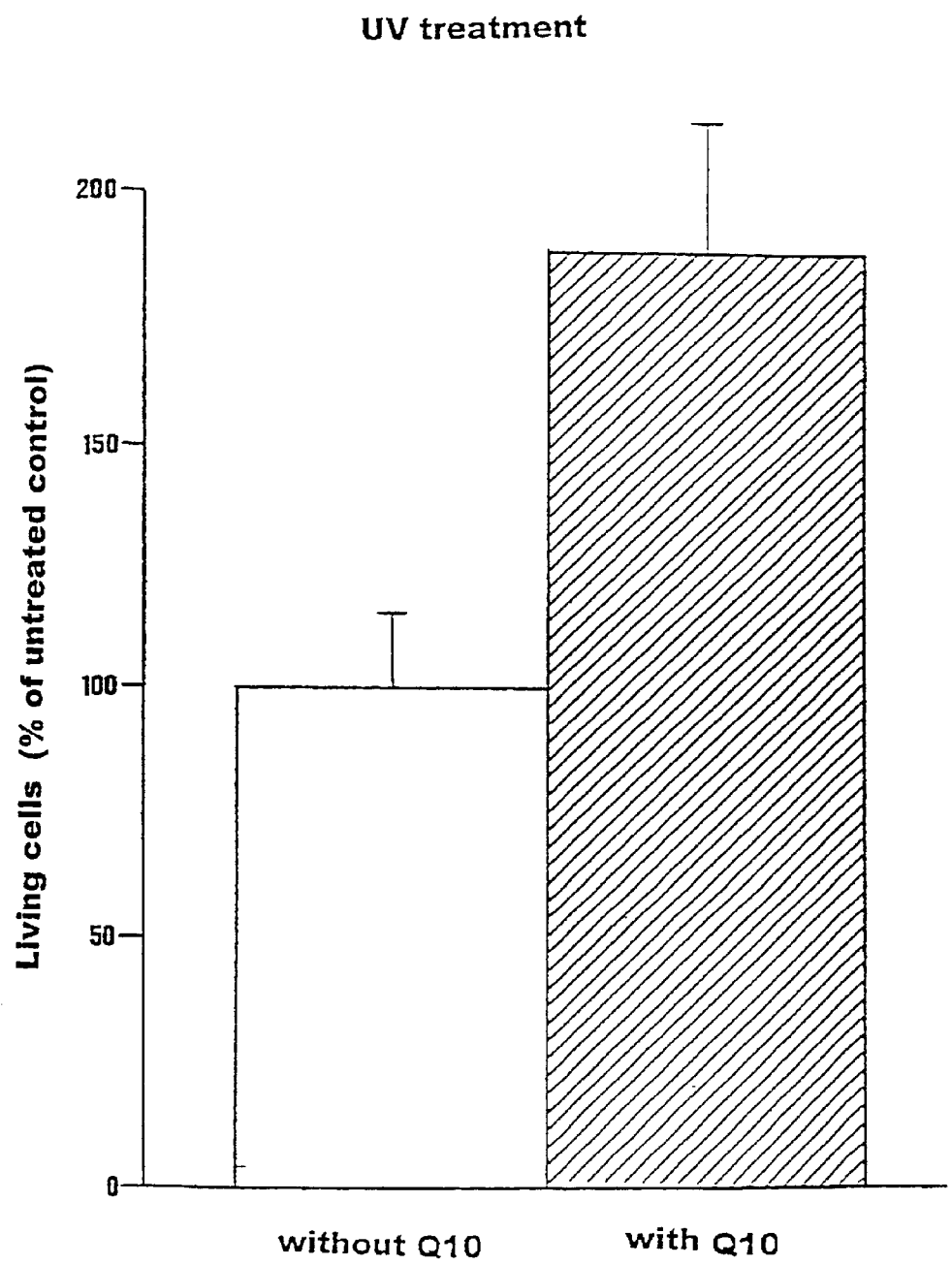
Figure 5B:
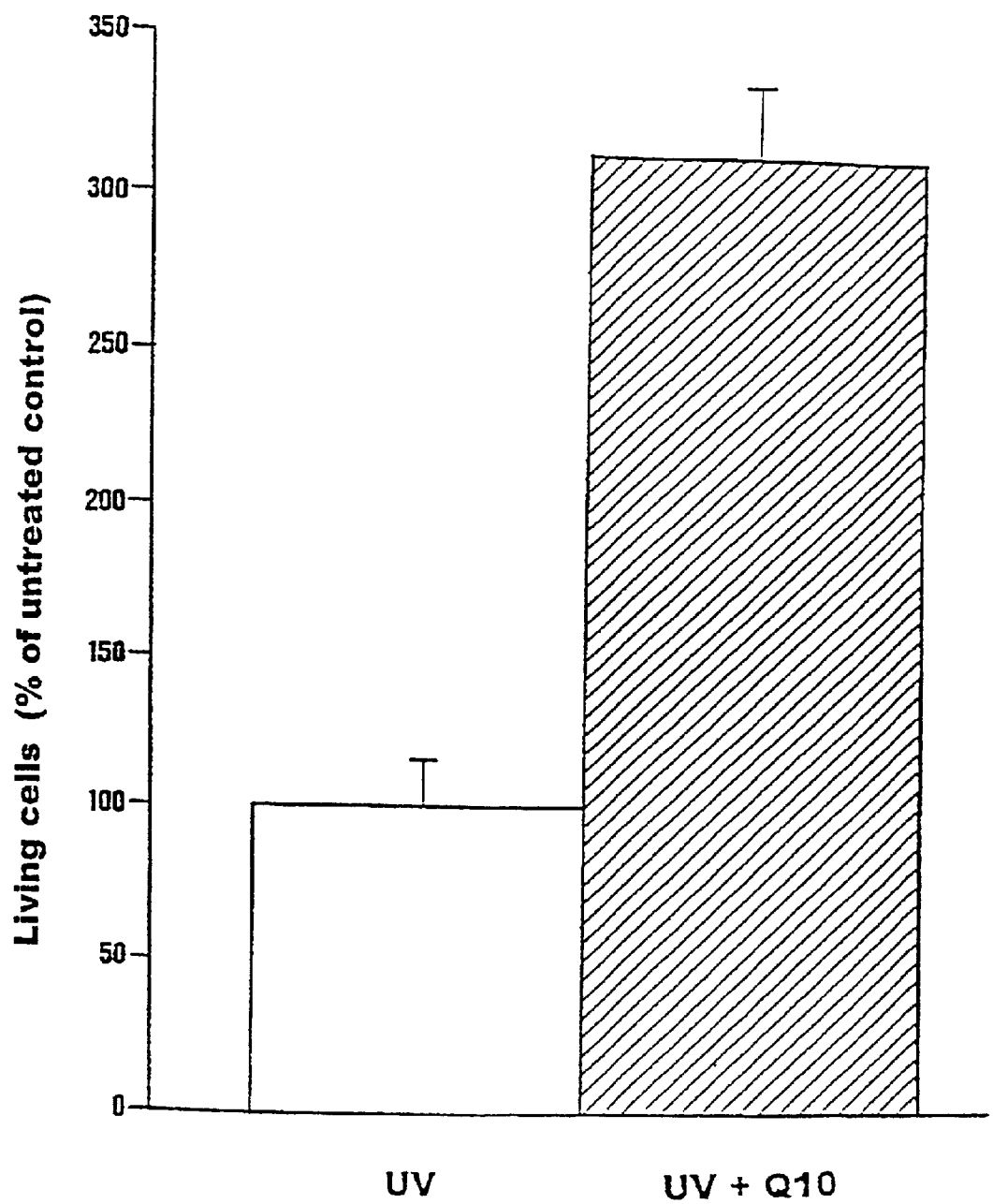
Figure 6A:
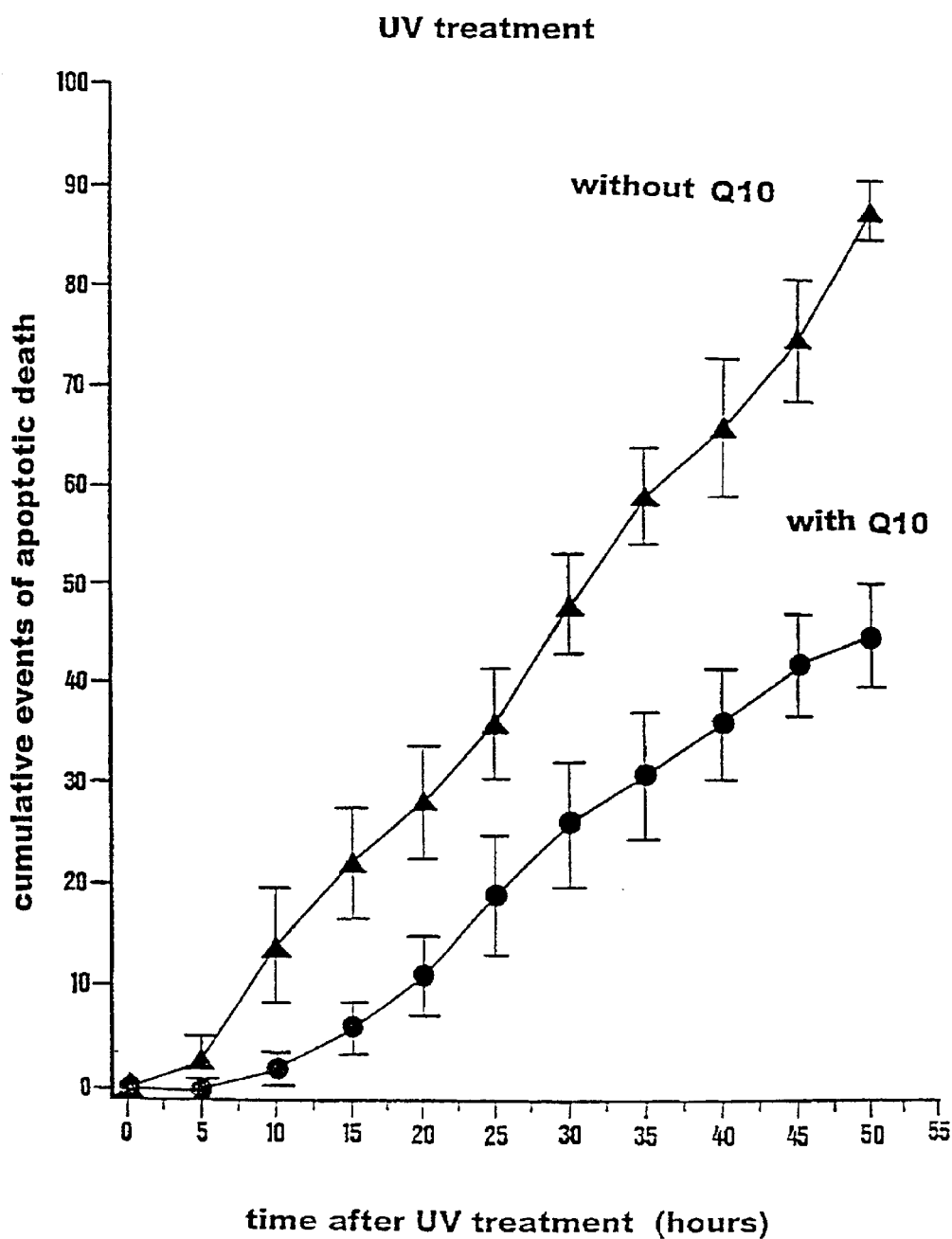
Figure 6B:
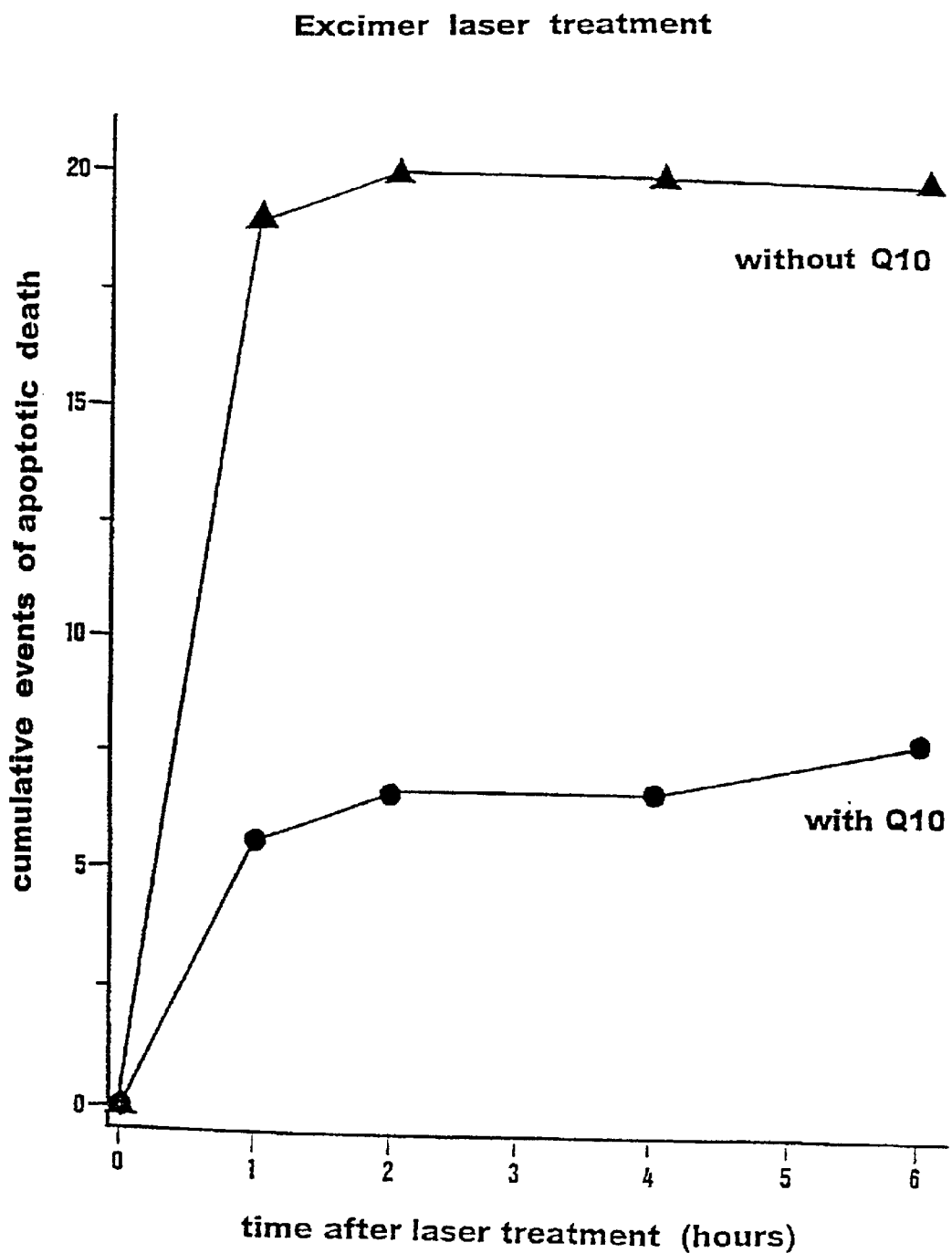

FIGS. 5a and 5b illustrate the Q10 protective effects according to the example 4, with respect to treatment with 25 nm UV radiation and with excimer laser respectively; and FIGS. 6a and 6b are diagrams illustrating the counting of vital cells according to what described in the example 4, following treatment with UV radiation and with excimer laser respectively.

EXAMPLE 1

Solubilization of Q10 in Solvent Suitable for the Administration in Culture Medium In a collyrium formulation for the Q10 administration, an essential step is to devise a vehicle, since the molecule is highly hydrophobic. To this purpose, a mother solution of Q10 2316 $\mu$M (0.2%) in Lutrol F127™ 10% in water has been prepared, with stirring. The solution has been then divided into parts of 500 $\mu$l each and the parts have been saturated by bubbling gaseous nitrogen therein and kept at 4° C. Upon use, the mother solution is further diluted by culture medium to obtain a daughter solution 100× (1000 $\mu$m). This solution has been utilized to treat in-plate cell cultures with the final Q10 concentration of 10 $\mu$M. In this way the final concentration of the vehicle (Lutrol F127™) in the culture medium is about 0.04%.

EXAMPLE 2

Figure 1A:
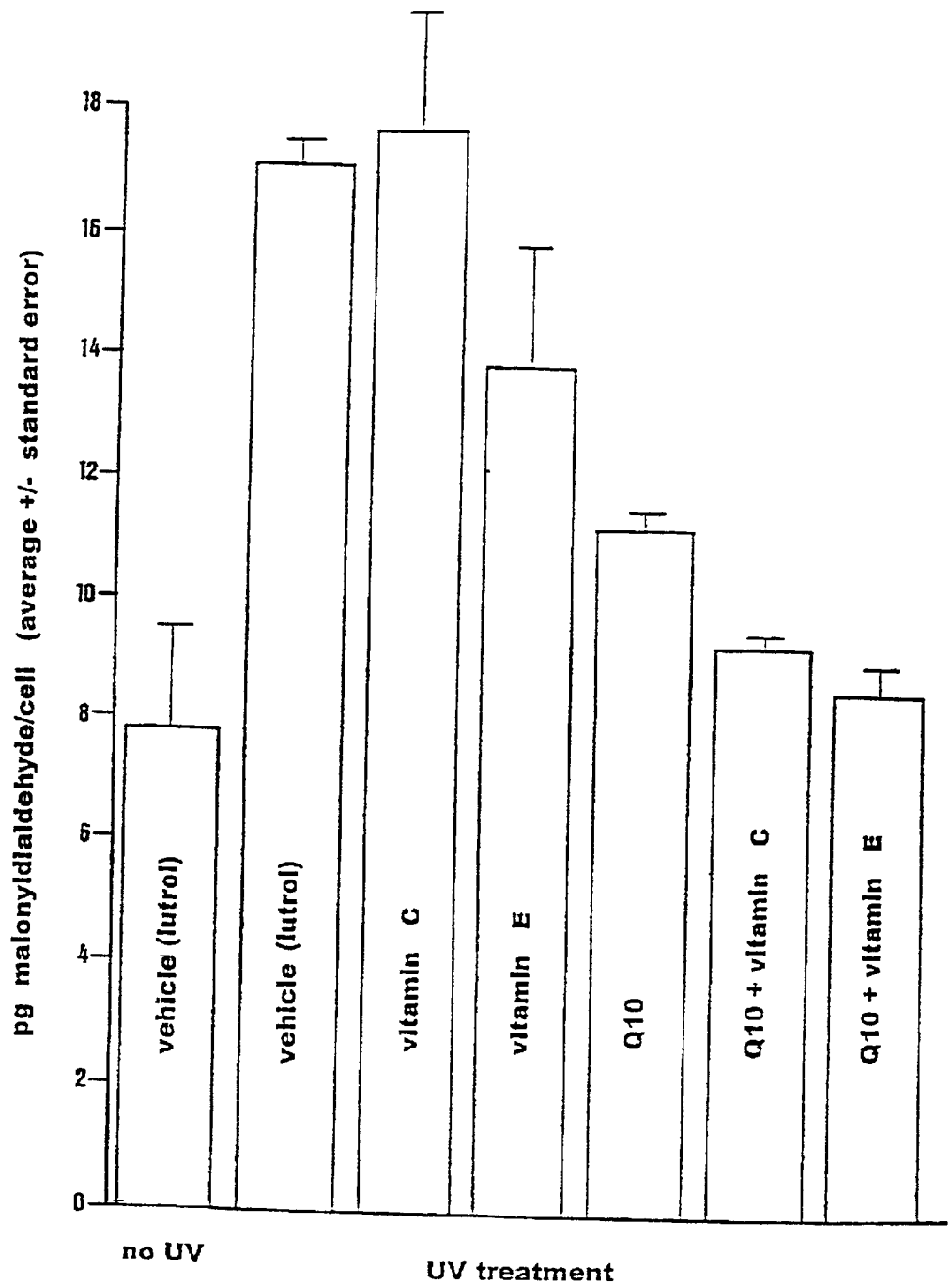
FIG. 1a is a diagram illustrating the malonaldehyde levels according to the example 2 following treatment with UV at 254 nm and in direct comparison with or without the utilization of vitamins, Q10 or both.
Figure 1B:
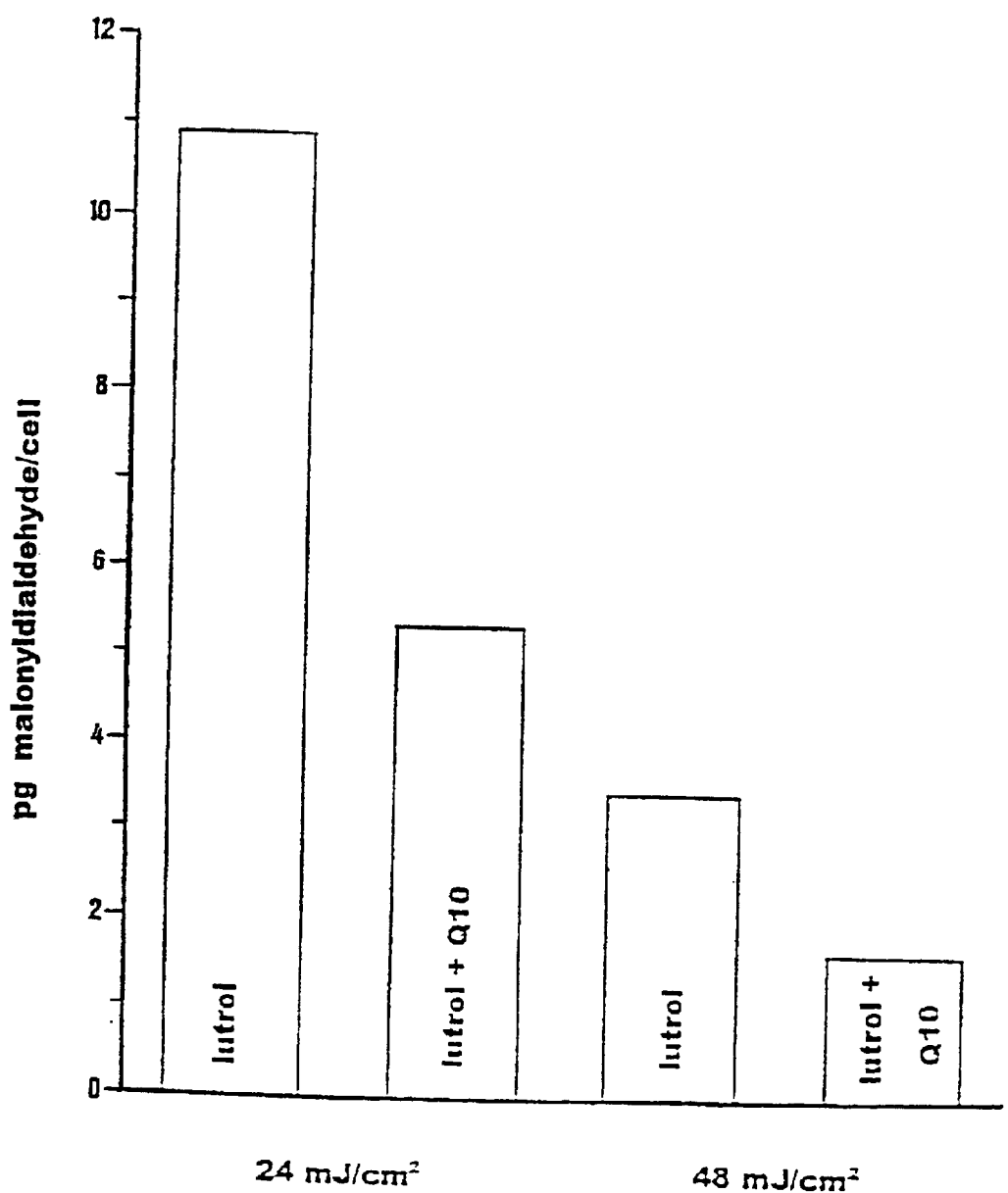
FIG. 1b is a diagram illustrating the malonaldehyde levels according the example 2 following treatment with 193 nm excimer laser and in direct comparison with or without the use of Q10.

Indirect Evaluation in the Production of Free Radicals following Treatment with 193 nm Excimer Laser and 254 nm Ultraviolet by Measuring the Malondialdehyde Levels and the Q10 Efficiency in Preventing It The malondialdehyde is a product of the lipid peroxidation which occurs following exposure to free radicals of polyinsaturated fat acids. The malondialdehyde production is then routinely interpreted as a production index of the radicals themselves by means of treatment with electromagnetic radiations or oxidant substances. The Q10, as antioxidant, decreases the malondialdehyde production by indicating an action thereof which inhibits the free radicals' formation. To perform the malondialdehyde assay, RCE cells (Rabbit Corneal Epithelial Cells which are rabbit corneal keratocytes immortalized with SV40) have been plated at the density of 5×10$^5$ cell/plate in 10 plates of Petri with 10-cm diameter and incubated overnight in 5% CO$_2$ atmosphere, 37° C. Then, the plates have been preincubated for 2 hours with Q10 10 $\mu$M, Vit.E, Vit. C dissolved in Lutrol F127™, alone or in combination and with Lutrol F127™ only, as shown in FIG. 1. Subsequently, the cells have been washed with 8 ml physiological saline buffered with sterile phosphate (PBS), additionated with Ca$^{++}$ e Mg$^{++}$ to avoid the cells detach from the support, and the dried up plates have been submitted to treatment with excimer laser ($\lambda$=194 nm) with various doses (as shown in FIG. 1$a$) or with 254 nm ultraviolet radiation (15,000 $\mu$J/cm$^2$), as shown in FIG. 1$b$. Subsequently the PBS has been replaced by fresh culture medium additionated with the above reagents and the plates have been incubated for further 2 hours. At the moment of the test the cells have been detached with trypsin according to standard procedures and counted by means of cell-counting chamber. Subsequently, the cells of various samples are lysed by adding trichloroacetic acid (TCA) and centrifugated for 20 minutes at 12,000 RPM in order to make proteins to precipitate.

At 300 $\mu$l of buffy coat of each sample, 300 $\mu$l of thiobarbituric acid (TBA) by 1% have been added. The mixtures have been incubated at 95° C. for 30 minutes, centrifugated for 20 minutes at 12,000 RPM and the optic absorption of the buffy coat resulting by spettrophotometric analysis at $\lambda$=532 nm has been assessed.

The obtained values have been compared with a calibration standard curve and normalized for the number of cells.

In FIG. 1$a$ the protective effect of Q10 alone or in combination with other antioxidants following treatment with UV radiation is shown.

The obtained values shown in the graph of FIG. 1$b$ show the Q10 reductive effect against the malondialdehyde production following treatment with various doses of 193 nm excimer laser radiation.

The experimentation demonstrates by direct comparison with other means of known art, the reduction performed by Q10 on the peroxidation level of the fat acids by free radicals and indirectly the protective effect against free radicals themselves produced by laser treatment.

EXAMPLE 3

Evaluation of the Adenosine Triphosphate (ATP) Levels Following Treatment with Excimer Laser and 254 nm Radiation, and of the Q10 Effect on Said Levels The ATP levels are strictly correlated to the cell death pattern which occurs following biochemical damage. For example an ATP level lower than 20% compared to normal value is responsible for necrosis whereas the higher levels still enable the occurrence of apoptosis which is notoriously a process requiring energy.

Whereas it has been checked that the ATP levels are going to be drastically reduced following treatment with radiation, it has resulted that, according to the present invention, the Q10 is able to prevent this reduction.

Figure 2A:
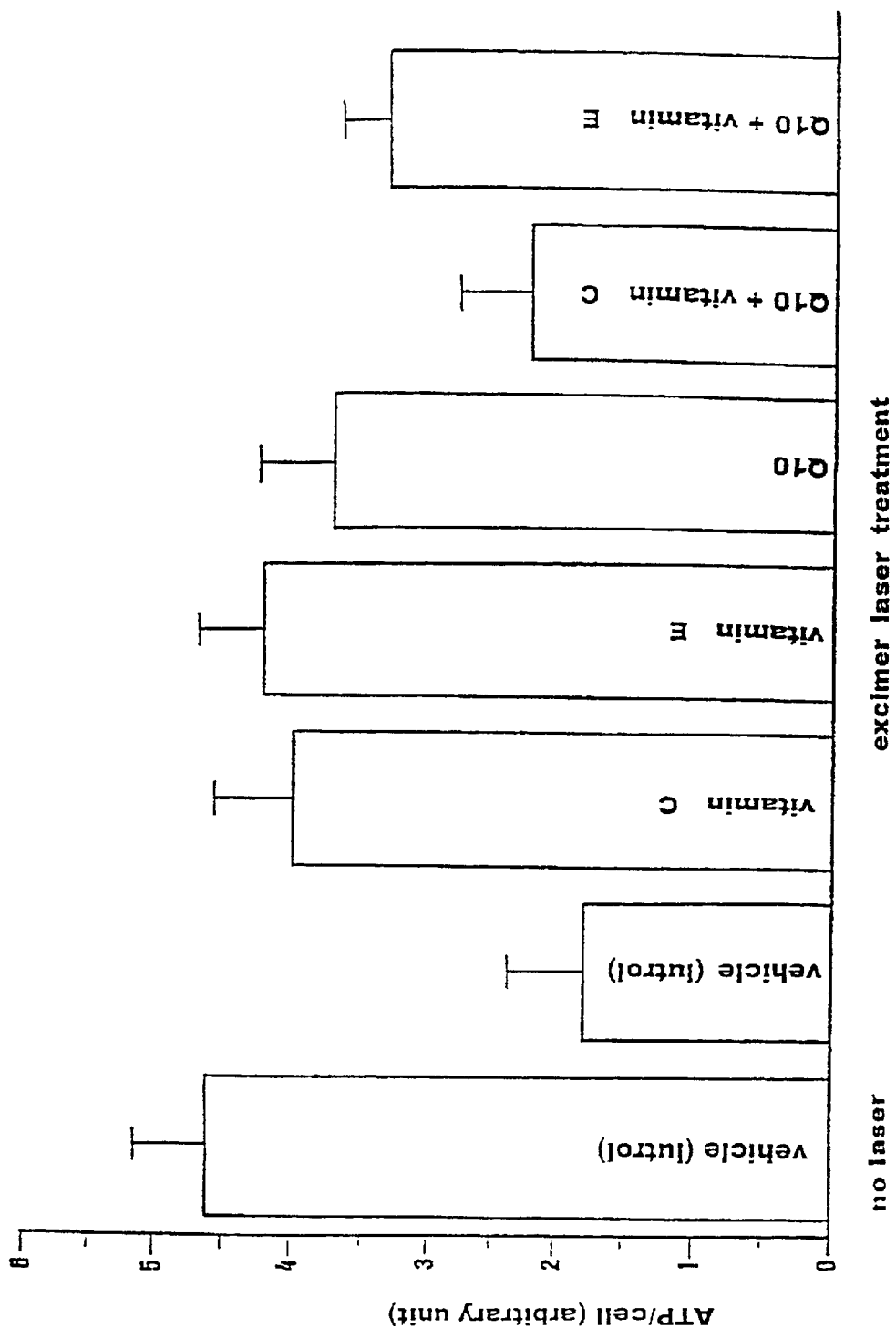
FIGS. 2a and 2b are diagrams illustrating the ATP levels according to the example 3 following treatment with excimer laser and with UV respectively.
Figure 2B:
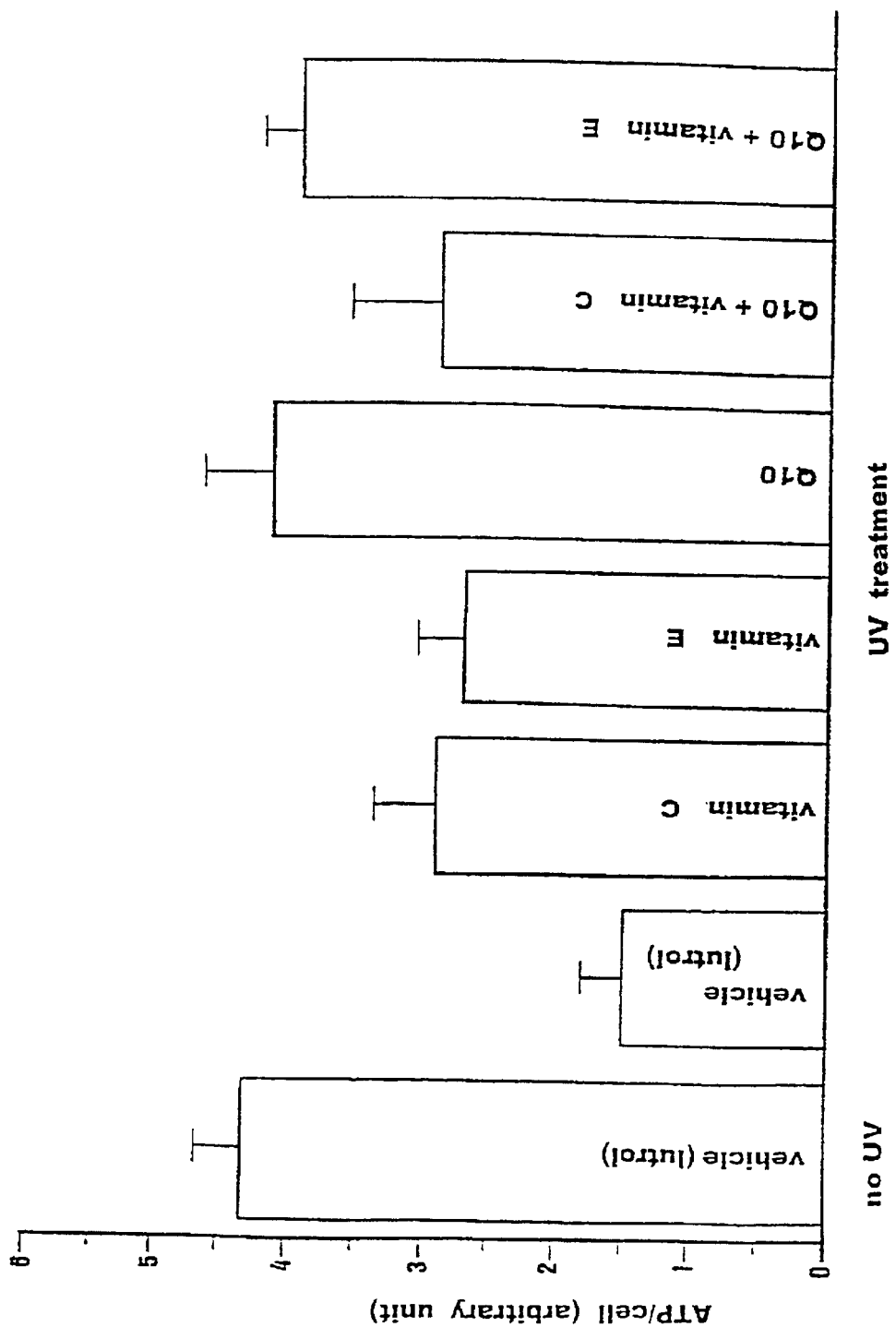

In order to perform the ATP test, RCE cells have been placed at the density of 5×10$^5$ cells/plate in 10 plates of Petri with 10-cm diameter and incubated overnight in 5% CO$_2$ atmosphere, 37° C. Subsequently the plates have been preincubated for 2 hours with Q10 at 10 $\mu$M dissolved in the Lutrol F127™ solution or with Lutrol F127™ only. The culture medium has been then replaced by 8 ml of sterile PBS, additionated with Ca$^{++}$ and Mg$^{++}$ to avoid the detach of the cells from the support and the plates have been submitted to treatment with excimer laser ($\lambda$=193 nm) as shown by FIG. 2$a$ or with 254 nm ultraviolet laser, as shown in FIG. 2$b$. Subsequently the PBS has been replaced by fresh culture medium additionated with the above reagents and the plates have been incubated for further 2 hours. At the moment of the assay the cells have been detached with trypsin according to standard procedures and counted by means of cell-counting chamber. The cells have been then resuspended in distille H$_2$O to a the concentration of 6×10$^4$ cells/1000 ml, immediately boiled for 5 minutes and frozen at −20° C. for subsequent analysis. The ATP quantification in the extracts has been performed by the "ATP Determination Kit" (Molecular Probes, USA) kit, based upon the firefly luciperase according to the supplier instructions. To detect fluorescence, an analyzer for liquid scintillation (Camberra Packard, USA) preset for the bioluminescence analysis has been utilized.

The experiment quantitatively demonstrates the Q10 protective effect opposing the decrease in the ATP level produced by UV radiation, with respect to a cell death of the necrotic pattern. This confirms the fact that the cell death pattern in presence of Q10 is moving towards etiologies different from those manifested in the absence thereof.

EXAMPLE 4

Counting of Vital Cells Following Treatment with 193 nm ArF Excimer Laser and 254 nm UV Radiation and Evaluation of the Q10 Protective Effect by Means of the Trypan Blue Exclusion Test on RCE Cells The counting of vital cells following a certain treatment period is an essential parametre in the evaluation of the radiation effects even if preliminary since it does not reveal anything about the fate the cells are going to (cell cycle block, apoptosis, necrosis). However, the fact that the Q10 has a general protection effect against death by radiation is an important data in preventing PDK collateral effects. In order to perform the trypan blue test, RCE cells have been plated at a density of $5 \times 10^5$ cells/plates with 10-cm diameter incubated overnight at 37° C., $CO_2$ 19%. Subsequently, the plates have been preincubated for 2 hours with Q10 10 $\mu$M dissolved in the Lutrol F127$^{MT}$ solution or with Lutrol F127™ only. The culture medium has been then replaced by 8 ml of sterile PBS, additioned with $Ca^{++}$ and $Mg^{++}$ to avoid the cell detachment from the support, and the plates have undergone treatment with excimer laser and $\lambda$=254 UV radiation in a Stratalinker apparatus, model 1800 (Stratagene). Subsequently the PBS has been replaced by fresh culture medium additioned with the above reagents. The plates have been incubated for the time shown in FIG. 6a and in FIG. 6b and subsequently detached by trypsin according to standard procedures and resuspended in PBS. To the cell suspension a trypan blue solution in PBS by 1% concentration has been added immediately before the counting performed by means of cell-counting chamber. The number of live cells is shown in the FIGS. 4, 5a and 5b in the non-treated sample percentage.

Figure 4:
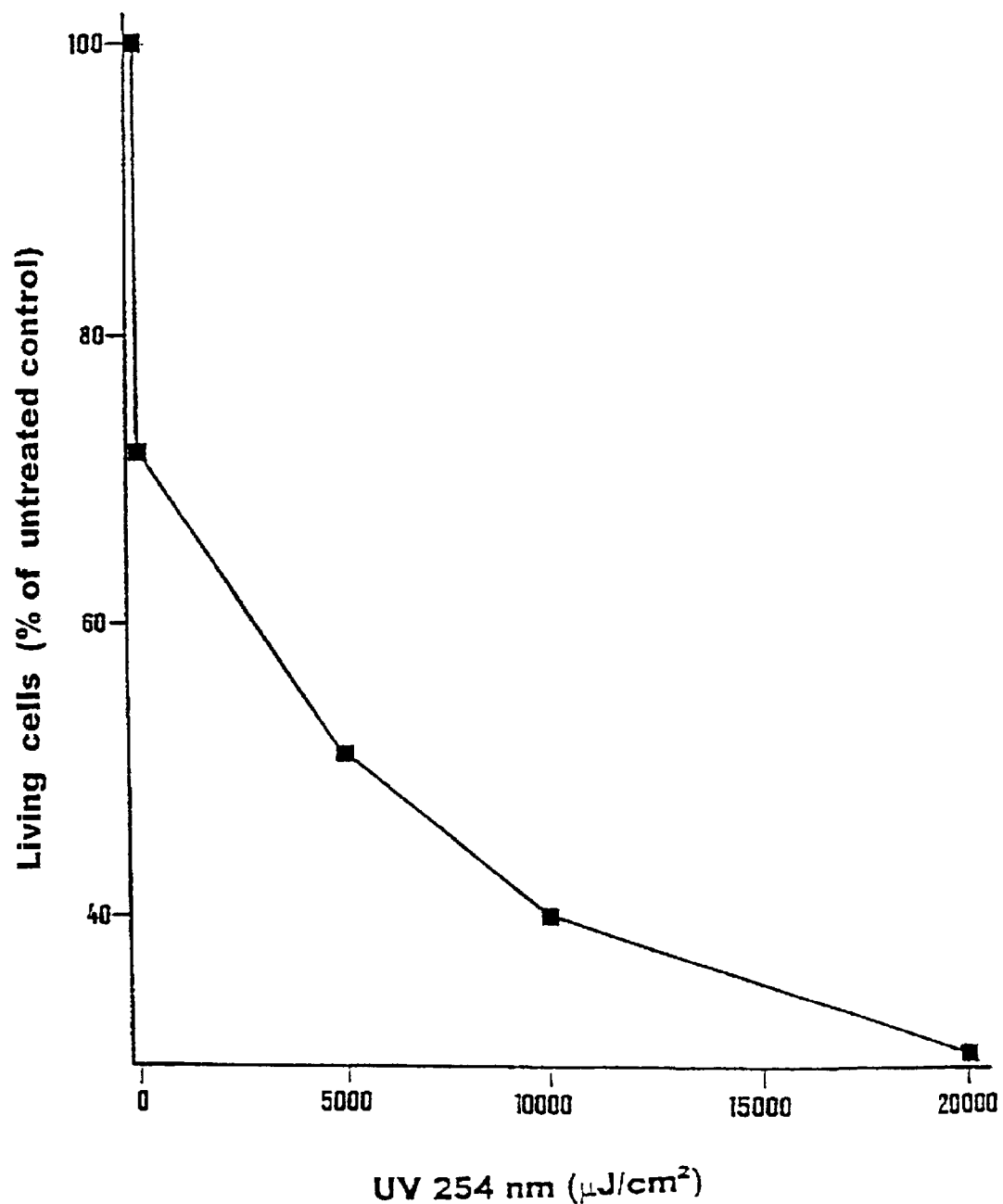
FIG. 4 is a diagram of the UV/response dose curve of vital cells by referring to the example 4.

FIG. 4 shows the UV dose/response curve according to which a 15,000 $\mu$J/cm$^2$ dose has been chosen for subsequent UV treatments so as to obtain the best apoptotic effects without moving away from the linearity range. For the excimer laser, a dose has been used comparable to the one that in vivo reaches the corneal layers involved by the previously described phenomena prejudicial to the eye. In the FIGS. 5a and 5b the Q10 protective effects against the damage by 254 nm UV radiation and by excimer laser respectively are shown.

The experiment of the example 4 demonstrates in a direct quantitative way the Q10 protective effect on the vitality of cells treated with excimer laser and 254 nm UV.

EXAMPLE 5

Quantitative Analysis in Optic Microscopy of the Q10 Protective Effect Against the Apoptosis Induced by 193 nm Excimer Laser RCE cells are treated as described in the following example 6.

Figure 3:
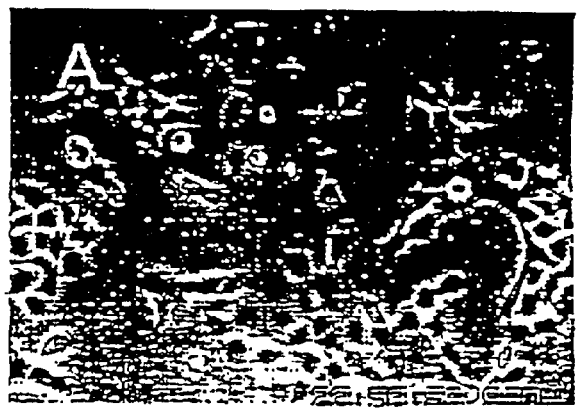
FIG. 3 shows three photograms A, B and C taken 24 hours after treatment of cells exposed to the above mentioned dose of 193 nm laser radiation, by referring to the example 5.
Figure 3:
Figure 3:
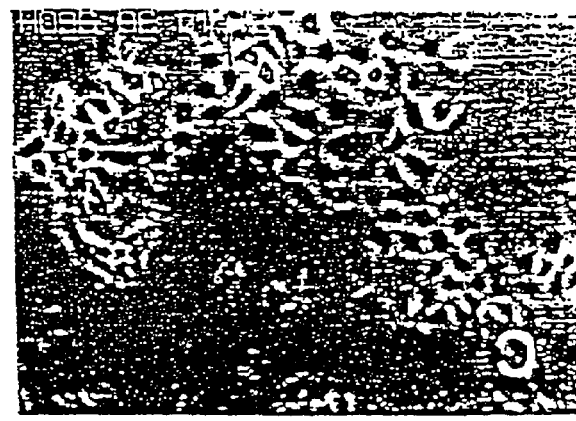

FIGS. 3A, 3B and 3C show photograms takes 24 hours after the treatment of cells exposed to the above mentioned dose of 193 nm laser radiation. The roundish refracting cells are collapsed cells detached by the typical apoptotic morphology.

EXAMPLE 6

Evaluation of the Q10 Antiapoptotic Effects by Means of Videomicroscopy at Time Intervals Following Treatment of RCE Cell with 93 nm Excimer Laser and 254 nm UV Radiation The videomicroscopy at time intervals is up to now one of the few techniques, if not the only one, enabling to have, apart from the cell death-type characterization, the exact quantification thereof too. In fact by continuously considering the cell population it is possible to calculate the number of cumulative deaths without losing any death event due to the disintegration of the cell body which typically occurs during apoptosis.

To perform the experiment RCE cells have been plated at the density of $5 \times 10^5$ cells/plate with 10-cm diameter and incubated overnight at 37° C., $CO_2$ 10%. Subsequently, the plates have been preincubated for 2 hours with Q10 10 $\mu$M dissolved in the Lutrol F127$^{MT}$ solution or with Lutrol F127™ only. The culture medium has been then replaced by 8 ml of sterile PBS, additioned with $Ca^{++}$ and $Mg^{++}$ to avoid the cell detachment from the support, and the plates have undergone treatment with excimer laser and $\lambda$=254 UV radiation in a Stratalinker apparatus, model 1800 (Stratagene) with various doses. Subsequently the PBS has been replaced by fresh culture medium additioned with the above reagents. The counting of individual apoptotic events, based upon the peculiar morphology of the apoptotic cell, has been continuously performed by means of videomicroscopy at time intervals by utilizing a self-assembled apparatus wherein Zeiss microscopes, Televal 31 model, time lapse Panasonic BR90300-type videorecorders and Panasonic video camera have been utilized in a range of 24–72 hours after treatment with radiation. Countings of the cumulative apoptotic deaths have been always performed by the same operator and are shown in graph vs. time (FIG. 6).

The example 6 demonstrates in a quantitative way and by direct reference to the apoptotic death pattern the Q10 protective effect on cells treated with 193 nm excimer laser and 254 nm UV radiation. The biochemical changes detected in the extracts of keratocytes treated with Q10 (ATP levels and malonaldehyde), as well as the phenotypical effects, show bona fide the occurred captation of the subject molecule by cells.

Topical Formulation for the Ubiquinone Ophthalmic Administration.
General Considerations.

As it is known, the poor solubility in water which is noticed in several pharmacologically active substances often leads to considerable formulative difficulties, especially when easily administrable aqueous solutions are desired. This occurs especially in the field of liquid preparations for topical ophthalmic use and for the use on oral mucosae.

By considering in a specific way the ophthalmic field, an active principle, to be therapeutically effective, has to be able to penetrate through the cornea and reach the action sites placed inside the eye. The cornea is a hydrophile-type structure, containing about 78% of water, collagen (12–15%) and proteoglycans (1–3%), soluble proteins, glucoproteins and a small part of lipids. It is then comprehensible that an active principle, if administered in an aqueous vehicle, more similar to the corneal structure, penetrates faster and in greater quantity inside the eye, by bringing about a prompter and more lasting therapeutic activity.

On the other side, there are several poorly hydrosoluble active principles which, on the contrary, would be extremely advantageous and efficient if administered by topical way in the form of collyria. As examples antiglaucoma agents (dapiprazole, forskolin), non-steroid anti-inflammatories (piroxicam, indomethacin), antioxidant agents (ubiquinone, tocopherol), antibacterials (amphotericin B, rufloxacin) may be mentioned. In all these cases the solubility in water of the active principle is so poor as to make impossible or not convenient the commercialization thereof in the form of collyrium, or to drastically limit the concentrations thereof in manufacturable preparations.

Several methods have been studied and devised during time to increase the solubility, and consequently the formulability and the bioavailability of poorly hydrosoluble drugs as well. These methods comprise chemical changes of insoluble molecule, solubilization by means of surfactants (micellar solutions), introduction in liposome vesiculae, complexation by means of polymers.

The transformation of the active principle into a ionic or ionizable derivative (for example an ester) is a very common solubilization method. Innumerable scientific publications have had as subject the micellar solubilization of drugs by means of surfactants. The micelle, for their lipophil-hydrophile feature, are able to mantain lipophilic products englobated in aqueous solution. A similar mechanism occurs with the use of liposomes, which are vesiculae able to encapsulate and contain inside thereof various types and quantities of molecules, even particularly lipophilic. The outer shell of liposomes shows instead strong hydrophilic features, so that it is easily dispersible in aqueous solution. The formation of complex, solutions and solid dispersions by using proper polymers is another method to increase the solubility in water of pharmaceutically active substances.

It is known that the Q10 coenzyme is a non-hydrosoluble substance and therefore the topical application thereof to the cornea in the form of aqueous collyrium has not been applied up to now in current technique.

The active agent ubiquinone Q10 may be for example vehiculated by means of a polyvinylpyrrolidone solution or by means of a cationic lipid in the form of liposome.

According to the present invention, a pharmaceutical form with innovative character for the ubiquinone vehiculation, both from the point of view of administration route and composition, has been surprisingly implemented. To the present state of art no ubiquinone-based preparation has been ever formulated for ophthalmic topical use, but the administration routes are limited to the cutaneous topic (in cosmetic preparations) or to oral systems.

The devised formulation enables the administration in the form of collyrium, as limpid and sterile aqueous solution, made isotonic by the lachrymal fluid. In the formulation even a liposoluble vitamin (tocopherol or Vitamin E in particular), with antioxidant activity, which can increase the stability of the active principle ubiquinone, has been introduced.

For the solubilization of the active principle, according to the present invention, a composition containing non-ionic surfactants has been utilized.

This composition comprises: ubiquinone Q10 by 0.01 up to 2.0% p/w; tocopherol by 0.005 up to 0.1% p/w; and a mixture including a modified castor oil and a block copolymer of hydrophilic ethylene oxide and lipophilic propylene oxide having a prevailing proportion of polyoxyethylene, an average molecular weight between 10,000 and 13,000 Dalton and a HLB value (hydrophile/lipophile equilibrium) higher than 15, in a quantity sufficient to solubilize said components in aqueous solution, generally between 10 and 15% p/w.

The mixture of these two surfactants (polyoxyethylene-polyoxypropylene) and a modified castor oil (poly-ethylene glycol glyceryl-triricinoleate), produces the full micellar solubilization of the components of the pharmaceutical form.

A particular example of the above-mentioned block copolymer is a commercial product called Lutrol F127.

The ubiquinone concentrations which may be utilized for the formulation of ophthalmic solutions are between 0.01 and 2.0% parts by weight (p/w); more preferably between 0.1 and 1.0% p/w, the ideal concentration as corneal "anti-haze" being understood by 0.2% p/w. The tocopherol concentrations in these preparations are generally between 0.005 and 0.1% p/w; more preferably between 0.01 and 0.5% p/w.

In a more particular way, a preferred composition comprises: ubiquinone Q10 by about 0.2% p/w; tocopherol by 0.02 up to 0.04% p/w; and the mixture including polyethylene glycol glyceryl-triricinoleate and an ethylene oxide/propylene oxide block polymer having a proportion of polyoxyethylene by about 70%, an average molecular weight of about 12,000 Dalton and a 22 HLB value.

The ingredient to be necessarily added to the formulations is a product causing the solution to have the right osmolar value. The solution containing the active principle only, in fact, results hypotonic compared to the lachrymal fluid. Other ingredients which may be added are pH correctors (comprising salts forming a buffer in the solution), products with antiseptic properties, complexants and preservatives, antioxidants and synergizing agents.

The process for the collyrium production comprises a process for the solubilization in water and in aqueous vehicles of ubiquinone (Q10 coenzyme). In particular, by means of the process, it is possible to highly increase the solubility in water of this compound in order to obtain aqueous solutions having concentrations useful from the therapeutic and commercial points of view.

Even in more details, the process enables to introduce in the same aqueous solution a liposoluble vitamin, which has per se an almost null solubility in water.

According to this process, ubiquinone, tocopherol, block copolymer, modified castor oil are melt at a temperature between 40 and 80° C., preferably 60° C. To the melt mass water at the same temperature (about 60° C.) is added under stirring. The dispersion is stirred to full solubilization of the components, then possible additives are added.

By way of example some formulation embodiments are listed:

| Ingredients | Concentration % p/w |
| --- | --- |
| Formulation 1 | |
| Ubiquinone | 0.20 |
| Tocopherol | 0.04 |
| Copolymer | 10.00 |
| Modified castor oil | 5.00 |
| NaCl | 0.45 |
| Benzalkonium chloride | 0.01 |
| Bidistilled water | q.s. to 100.00 |
| Formulation 2 | |
| Ubiquinone | 0.10 |
| Tocopherol | 0.02 |
| Copolymer | 15.00 |
| Mannitol | 2.50 |
| Benzalkonium chloride | 0.01 |
| Bidistilled water | q.s. to 100.00 |
| Formulation 3 | |
| Ubiquinone | 0.20 |
| Copolymer | 10.00 |
| NaCl | 4.50 |
| Benzalkonium chloride | 0.01 |
| Phosphate buffer Sorensen pH | 7.4 |
| quantum sufficit to | 100.00 |

Even if the present invention has been described in details, it is intended that variations and changes may be derived therefrom within the scope and spirit of the invention itself.

What is claimed is:

1. A method for the prevention and treatment of incidental or post-surgical trauma pathologies of the anterior chamber of the eye comprising administering to a patient, via topical ophthalmic application, a collyrium medicament comprising coenzyme ubiquinone Q10.

2. The method according to claim 1, wherein the prevention and treatment of incidental or post-surgical trauma comprises prevention and treatment of corneal haze following corneal trauma, general surgery and refractive surgery; prevention of regression of corrective effects after operation of refractive surgery performed by conventional surgery or by laser radiation; and eye protection against damage determined by solar light and ultraviolet radiation.

3. The method according to claim 2, wherein the prevention and treatment of incidental or post-surgical trauma is directed to protect eye cells against reversible or irreversible damage induced by said surgical operation and/or laser and by exposure to solar and ultraviolet radiation.

4. The method according to claim 3, wherein said irreversible damage of said cells is apoptosis.

5. The method according to claim 4, wherein said cells are corneal stromal keratocytes.

6. The method according to claim 5, wherein said refractive surgery is the photorefractive keratectomy (pRK) and the laser-assisted in situ keratomileusis (LASIK).

7. The method according to claim 6, wherein said photorefractive keratectomy (pRK) and said laser-assisted in situ keratomileusis (LASIK) are performed by laser sources.

8. The method according to claim 7, wherein said laser sources are excimer laser.

9. The method according to claim 8, wherein said laser source is a 193 nm ArF excimer laser.

10. The method according to claim 3, wherein said medicament is administered to the patient via topical ophthalmic application to the cornea and wherein said medicament comprises a composition including ubiquinone Q10 in a quantity effective to said treatment and a pharmaceutically compatible vehicle.

11. The method according to claim 10, wherein said vehicle is an aqueous solution of a mixture comprising: a block copolymer of hydrophilic ethylene oxide and lipophilic propylene oxide, having a prevailing proportion of polyoxyethylene, an average molecular weight between 10,000 and 13,000 Dalton and a HLB value higher than 15; and a polyoxyethylene-modified castor oil.

12. The method according to claim 11, wherein said copolymer comprises about 70% of polyoxyethylene and has a HLB value of about 22.0.

13. The method according to claim 11 or 12, wherein said polyoxyethylene-modified castor oil is polyethylene glycol glyceryl-triricinoleate.

\* \* \* \* \*